US00PP23369P2

(12) United States Plant Patent
Koning

(10) Patent No.: US PP23,369 P2
(45) Date of Patent: Jan. 29, 2013

(54) ***VIOLA* PLANT NAMED 'BLACKOUT'**

(50) Latin Name: *Viola cornuta*
Varietal Denomination: Blackout

(76) Inventor: Lammert Koning, Nuis (NL)

( * ) Notice: Subject to any disclaimer, the term of this patent is extended or adjusted under 35 U.S.C. 154(b) by 38 days.

(21) Appl. No.: 13/136,133

(22) Filed: Jul. 25, 2011

(51) Int. Cl.
*A01H 5/00* (2006.01)

(52) U.S. Cl. ..... Plt./323

(58) Field of Classification Search ..... Plt./323
See application file for complete search history.

*Primary Examiner* — Susan McCormick Ewoldt

(74) *Attorney, Agent, or Firm* — Audrey Charles

(57) ABSTRACT

A new and distinct cultivar of *Viola* plant named 'Blackout', characterized by its deep black colored flowers, medium green-colored foliage, low growth vigor, and outwardly-spreading, mounded growth habit, is disclosed.

1 Drawing Sheet

Latin name of genus and species of plant claimed: *Viola cornuta.*

Variety denomination: 'Blackout'.

BACKGROUND OF THE INVENTION

The present invention relates to a new and distinct cultivar of *Viola* plant botanically known as *Viola cornuta* and hereinafter referred to by the cultivar name 'Blackout'.

The new cultivar originated in a controlled breeding program in Westerbork, The Netherlands during March 2008. The objective of the breeding program was the development of *Viola* cultivars with high floriforousness, attractive black flower coloration, medium green-colored foliage, and outwardly-spreading, mounded growth habit.

The new *Viola* cultivar is the result of cross-pollination. The female (seed) parent of the new cultivar is the 'Molly Sanderson', not patented, characterized by its black-colored flowers, medium green-colored foliage, and compact-spreading growth habit. The male (pollen) parent of the new cultivar is 'Highland Black', not patented, characterized by its black-colored flowers, medium green-colored foliage, and upright growth habit. The new cultivar was discovered and selected as a single flowering plant within the progeny of the above stated cross-pollination during March 2009 in a controlled environment in Westerbork, The Netherlands.

Asexual reproduction of the new cultivar by terminal stem cuttings since March 2009 at Westerbork, The Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Blackout' as a new and distinct cultivar of *Viola* plant:

1. Deep black colored flowers;
2. Medium green-colored foliage;
3. Low growth vigor; and
4. Outwardly-spreading, mounded growth habit.

Plants of the new cultivar differ from plants of the female and male parents primarily in purity of flower color and growth habit. The new cultivar has deeper black-colored flowers than either parent.

Of the many commercially available *Viola* cultivars, the most similar in comparison to the new cultivar is 'Black Magic', expired U.S. Plant Pat. No. 6,595. However, in side-by-side comparison, plants of the new cultivar differ from plants of 'Black Magic' in at least the following characteristics:

1. Plants of the new cultivar have peduncles that are longer and have a larger diameter than plants of 'Black Magic';
2. Plants of the new cultivar have larger leaves, as measured by leaf width, than plants of 'Black Magic';
3. Plants of the new cultivar have a lighter colored corolla spur than plants of 'Black Magic'; and
4. Plants of the new cultivar have larger flowers, as measured by corolla width, than plants of 'Black Magic'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Blackout'. The plants were grown in 6-inch pots for 12 weeks in a greenhouse at Elburn, Ill. Plants were given one pinch at transplant.

DETAILED BOTANICAL DESCRIPTION

Figure 1:
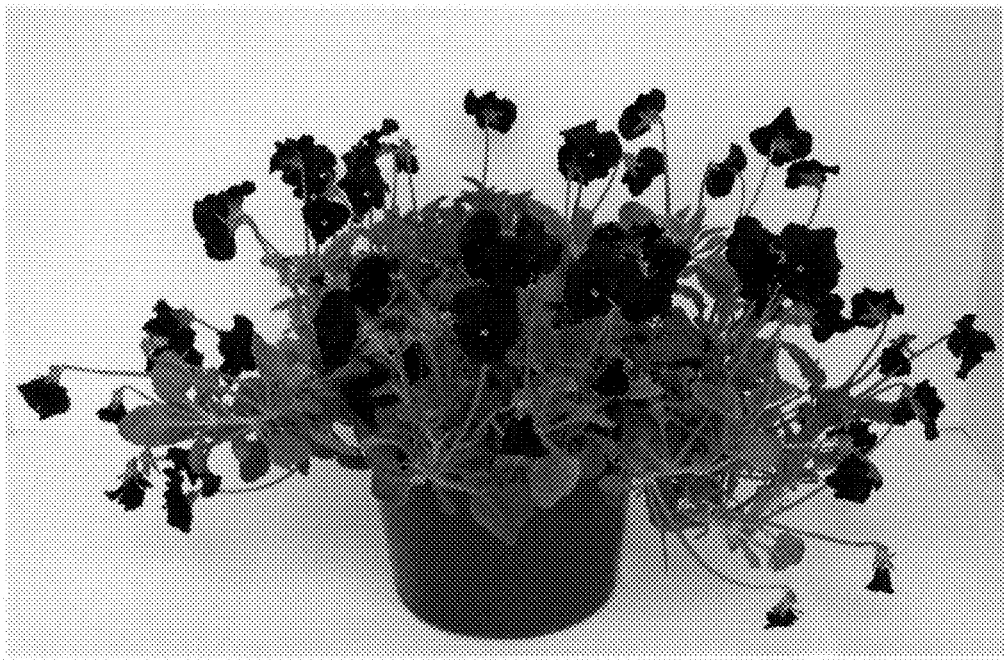
FIG. 1 illustrates a side view of the overall growth and flowering habit of 'Blackout'.
Figure 2:
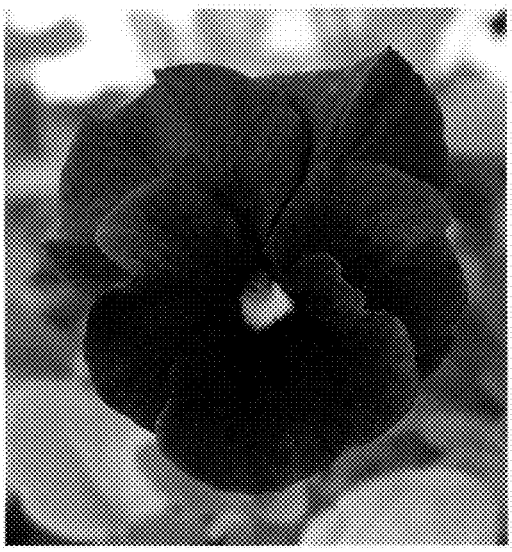
FIG. 2 illustrates a close-up view of an individual flower of 'Blackout'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2011 under natural light conditions in West Chicago, Ill.

The following descriptions and measurements describe plants produced from cuttings from stock plants and grown in a glass-covered greenhouse under conditions comparable to those used in commercial practice. The plants were grown in Elburn, Ill. in 6-inch pots for 12 weeks utilizing a soilless growth medium. Plants were given one pinch at transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Viola cornuta* cultivar Blackout.

Parentage:

*Female parent*.—'Molly Sanderson', not patented.

*Male parent*.—'Highland Black', not patented.

Propagation:

*Type cutting*.—Terminal stem.

*Time to initiate roots*.—Approximately 10 to 12 days.

*Time to produce a rooted cutting*.—Approximately 24 to 28 days.

*Root description*.—Fine, fibrous.

*Rooting habit*.—Freely branching.

Plant description:

*Commercial crop time*.—Approximately 8 to 10 weeks from a rooted cutting to finish in a 10 cm pot.

*Growth habit and general appearance*.—Low growth vigor, outwardly-spreading, mounded growth habit.

*Size*.—Height from soil level to top of plant plane: Approximately 14.5 cm. Width: Approximately 34.0 cm.

*Branching habit*.—Freely branching, pinching enhances branching. Quantity of main branches per plant: Approximately 27.

*Lateral branches*.—Strength: Strong, flexible. Length: Approximately 14.5 cm. Diameter: Approximately 3.0 mm. Length of central internode: Approximately 1.3 cm. Texture: Pubescent. Color of young and mature stems: 144B.

Foliage description:

*General description*.—Quantity of leaves per main branch: Approximately 18. Fragrance: None. Form: Simple. Arrangement: Alternate.

*Leaves*.—Aspect: Petiole is at an acute angle to stem and leaf blade is nearly perpendicular to stem. Shape: Narrowly ovate. Margin: Crenate. Apex: Obtuse. Base: Rounded to truncate. Venation pattern: Pinnate. Length of mature leaf at center of stem: Approximately 2.7 cm. Width of mature leaf at center of stem: Approximately 2.0 cm. Texture of upper and lower surfaces: Glabrous. Color of upper surface of young foliage: 137B with venation 137D. Color of lower surface of young and mature foliage: Closest to 138B with venation similar to lamina. Color of upper surface of mature foliage: 137A with venation 137D.

*Petiole*.—Length: Approximately 2.1 cm. Diameter: Approximately 1.0 mm. Texture: Glabrous. Color: 144A.

*Stipules*.—Shape: Narrowly Ovate. Margin: Cleft. Apex: Obtuse. Base: Attenuate. Length: Approximately 2.5 cm. Width: Approximately 1.2 cm. Texture of upper surface: Glabrous. Texture of lower surface: Glabrous. Color of upper surface: 137A. Color of lower surface: 138B.

Flowering description:

*Flowering habit*.—'Blackout' is freely flowering under outdoor growing conditions with substantially continuous blooming from spring through autumn and with limited flowering under short winter days in a greenhouse environment.

*Lastingness of individual flower on the plant*.—Approximately 4 to 5 days.

Flower description:

*General description*.—Type: Single, zygomorphic, not persistent. Flower aspect: Pendant. Quantity per plant: Approximately 60. Fragrance: Slightly sweet.

*Bud*.—Rate of opening: Generally takes 2 to 3 days for bud to progress from first color to fully open flower. Quantity showing color per plant: Approximately 9.

*Bud just before opening*.—Shape: Oblong. Length: Approximately 1.9 cm. Diameter: Approximately 6.0 mm. Color: 203D.

*Corolla*.—Shape: Orbicular, with a spur on lower petal. Length: Approximately 3.1 cm. Width: Approximately 3.0 cm. Depth: Approximately 1.7 cm.

*Petals*.—Quantity: 5. Shape of upper petals: Widely ovate. Shape of lateral petals: Widely ovate. Shape of lower petal: Fan-shaped. Appearance: Dull. Margin of all petals: Entire, slightly ruffled. Apex of upper and lateral petals: Obtuse. Apex of lower petal: Rounded. Base of upper and lateral petals: Widely attenuate. Base of lower petal: Truncate. Length of upper petals: Approximately 1.5 cm. Width of upper petals: Approximately 2.0 cm. Length of lateral petals: Approximately 1.9 cm. Width of lateral petals: Approximately 1.7 cm. Length of lower petal: Approximately 1.4 cm. Width of lower petal: Approximately 2.1 cm. Texture of upper surface of all petals: Glabrous, with base of lateral petals densely glandular pubescent. Color of pubescence: N88A. Texture of lower surface of all petals: Glabrous. Color of upper surface of upper and lateral petals when first and fully open: 202A. Color of lower surface of upper and lateral petals when first and fully open: 202A. Color of upper surface of lower petal when first and fully open: 202A with 13A at base. Color of lower surface of lower petal when first and fully open: 202A.

*Spur*.—Quantity: 1 per flower on lower petal. Length: Approximately 7.0 mm. Diameter at proximal end: Approximately 2.0 mm. Diameter at distal end: Approximately 1.0 mm. Color: 155C with an overlay of N88C.

*Calyx*.—Shape: Stellate. Diameter: Approximately 1.6 cm.

*Sepals*.—Quantity per flower: 5. Shape: Lanceolate. Margin: Entire. Apex: Acute. Base: Rounded. Length: Approximately 1.1 cm. Width: Approximately 3.0 mm. Texture of upper and lower surfaces: Glabrous. Color of upper and lower surfaces: 138C.

*Peduncle*.—Shape: Square in cross section. Strength: Moderately strong. Aspect: Acute angle to stem. Length: Approximately 9.6 cm. Diameter: Approximately 2.0 mm. Texture: Glabrous. Color: 144A.

*Reproductive organs*.—Androecium: Stamen quantity: 5 per flower. Stamen arrangement: Tightly appressed against ovary. Stamen length: 3.0 mm. Two bear nectar spurs of 3.0 mm in length. Anther shape: Ellipsiodal. Anther length: Approximately 2.5 mm. Anther width: Approximately 1.5 mm. Anther color: 158D. Pollen amount: Sparse. Pollen color: 4D. Gynoecium: Pistil quantity: 1 per flower. Pistil length: Approximately 4.0 mm. Stigma shape: Globular. Stigma length: 1.0 mm. Stigma color: N144D. Style color: 144D. Ovary shape: Ovoid. Ovary position: Superior. Ovary diameter: 2.0 mm. Ovary color: 144C.

Seed and fruit production: Neither seed nor fruit production has been observed.

Disease and pest resistance: Resistance to pathogens and pests common to *Viola* has not been observed.

What is claimed is:

1. A new and distinct cultivar of *Viola* plant named 'Blackout', substantially as herein shown and described.

* * * * *